United States Patent [19]

Riise

[11] Patent Number: 4,632,764
[45] Date of Patent: * Dec. 30, 1986

[54] SLUDGE DEWATERING PROCESS USING MULTIPLE LAYER PLATE

[75] Inventor: Morris M. Riise, Miami Beach, Fla.

[73] Assignee: International Sludge Reduction Company, Fort Lauderdale, Fla.

[*] Notice: The portion of the term of this patent subsequent to May 10, 2000 has been disclaimed.

[21] Appl. No.: 629,722

[22] Filed: Jul. 11, 1984

Related U.S. Application Data

[60] Continuation of Ser. No. 379,758, May 19, 1982, abandoned, Division of Ser. No. 202,241, Oct. 30, 1980, Pat. No. 4,382,862, which is a continuation of Ser. No. 098,887, Nov. 30, 1979, abandoned, which is a continuation of Ser. No. 930,529, Aug. 2, 1978, abandoned, which is a continuation-in-part of Ser. No. 739,602, Nov. 8, 1976, abandoned.

[51] Int. Cl.$^4$ ............... C02F 1/52; B01D 23/02
[52] U.S. Cl. .................... 210/702; 210/769; 210/791; 210/800
[58] Field of Search ............... 210/169, 187, 259, 271, 210/290, 293, 416, 506, 510, 490, 504, 510.1, 702, 729, 732, 769, 791, 800; 428/403, 407, 408; 379/758

[56] References Cited

U.S. PATENT DOCUMENTS

| | | | |
|---|---|---|---|
| 421,238 | 2/1890 | Bush et al. | 210/510 |
| 624,893 | 5/1899 | Davis | 210/498 |
| 730,518 | 6/1903 | Davis | 210/498 |
| 931,032 | 8/1909 | Bussman | 210/170 |
| 1,081,573 | 12/1913 | Boeck | 210/510 |
| 1,117,601 | 11/1914 | Porter | 210/510 |
| 1,277,832 | 9/1918 | Beckley | 210/293 |
| 1,543,939 | 6/1925 | Maclachlan | 210/702 |
| 1,671,325 | 5/1928 | Straub . | |
| 1,884,528 | 10/1932 | Benner et al. . | |
| 1,910,758 | 5/1933 | Dundore | 210/506 |
| 1,918,893 | 7/1933 | Beckmann | 210/506 |
| 1,987,721 | 1/1935 | Straub | 25/155 |
| 1,988,478 | 1/1935 | Broadwell et al. | 210/506 |
| 2,018,192 | 10/1935 | Sexton | 25/155 |
| 2,155,016 | 4/1939 | Kershaw | 18/53 |
| 2,293,099 | 8/1942 | Barnes et al. | 25/156 |
| 2,303,629 | 12/1942 | Gelinas | 210/205 |
| 2,335,749 | 11/1943 | Fraser | 210/271 |
| 2,345,827 | 4/1944 | Olin | 210/702 |
| 2,464,517 | 3/1949 | Kurtz | 210/510 |
| 2,597,217 | 5/1952 | Zenick | 210/166 |
| 2,732,078 | 1/1956 | Records | 210/510 |
| 3,011,643 | 12/1961 | McCoy | 210/169 |
| 3,056,704 | 10/1962 | Rothweiler et al. | 154/216 |
| 3,166,615 | 1/1965 | Farrell | 264/23 |

(List continued on next page.)

FOREIGN PATENT DOCUMENTS 176849 11/1953 Austria ................... 210/510

OTHER PUBLICATIONS

"Filtros Underdrain Plates" Bulletin, from Filtros, Inc., East Rochester, New York 5/29/63.
Hackh's Chemical Dictionary (4th ed.), p. 596, J. Grant Editor, McGraw-Hill Book Co., N.Y., 1969.

Primary Examiner—David Sadowski
Attorney, Agent, or Firm—Allegretti, Newitt, Witcoff & McAndrews, Ltd.

[57] ABSTRACT

A system for rapidly dewatering sludge in large quantities makes use of a filter plate that is capable of supporting heavy mechanized removal equipment without damage to the filter plate. The filter plate is monolithic and includes granular filter material that is rigidified and bonded together. In the disclosed process, sludge is pretreated with a polymer coagulant that breaks up solids and flocculates the sludge particles. The flocculated sludge is then spread on a bed of filter plates. As the bed is being filled, the large coagulated sludge particles settle and water is drawn off by gravity. A vacuum is then applied to the bed and the sludge is rapidly dewatered. Upon completion of dewatering, front end loading equipment may be used to remove the dried sludge cake from the bed.

7 Claims, 12 Drawing Figures

U.S. PATENT DOCUMENTS

| | | | |
|---|---|---|---|
| 3,171,804 | 3/1965 | Rice | 210/702 X |
| 3,178,026 | 4/1965 | Christy | 210/293 |
| 3,196,105 | 7/1965 | Schneider | 210/187 |
| 3,279,606 | 10/1966 | Cox | 210/187 |
| 3,545,622 | 12/1970 | Sakhnovsky | 210/496 |
| 3,587,861 | 6/1971 | Ross | 210/277 |
| 3,615,019 | 10/1971 | Early, Jr. | 210/293 |
| 3,630,384 | 12/1971 | Toda | 210/506 |
| 3,716,459 | 2/1973 | Salter et al. | 204/1 R |
| 3,771,655 | 11/1973 | Hudson, Jr. | 210/108 |
| 3,779,910 | 12/1973 | Chatfield | 210/738 X |
| 3,847,808 | 11/1974 | Spohr | 210/271 |
| 3,959,126 | 5/1976 | Millward | 210/764 X |
| 3,969,248 | 7/1976 | Whitmer | 210/126 |
| 4,081,371 | 3/1978 | Yarwood et al. | |
| 4,088,576 | 5/1978 | Mott | 210/510 X |
| 4,186,100 | 1/1980 | Mott | 210/496 |
| 4,190,534 | 2/1980 | Wyatt | 210/271 |
| 4,208,288 | 6/1980 | Stannard et al. | 210/277 |
| 4,309,292 | 1/1982 | Stannard et al. | 210/792 |
| 4,340,478 | 7/1982 | Stannard et al. | 210/286 |
| 4,381,998 | 5/1983 | Roberts et al. | 210/503 |
| 4,382,863 | 5/1983 | Riise | 210/702 |
| 4,399,042 | 8/1983 | Stannard et al. | 210/791 |
| 4,431,549 | 2/1984 | Highstreet et al. | 210/791 |
| 4,452,698 | 6/1984 | Roberts et al. | 210/503 |
| 4,481,114 | 11/1984 | Riise | 210/702 |

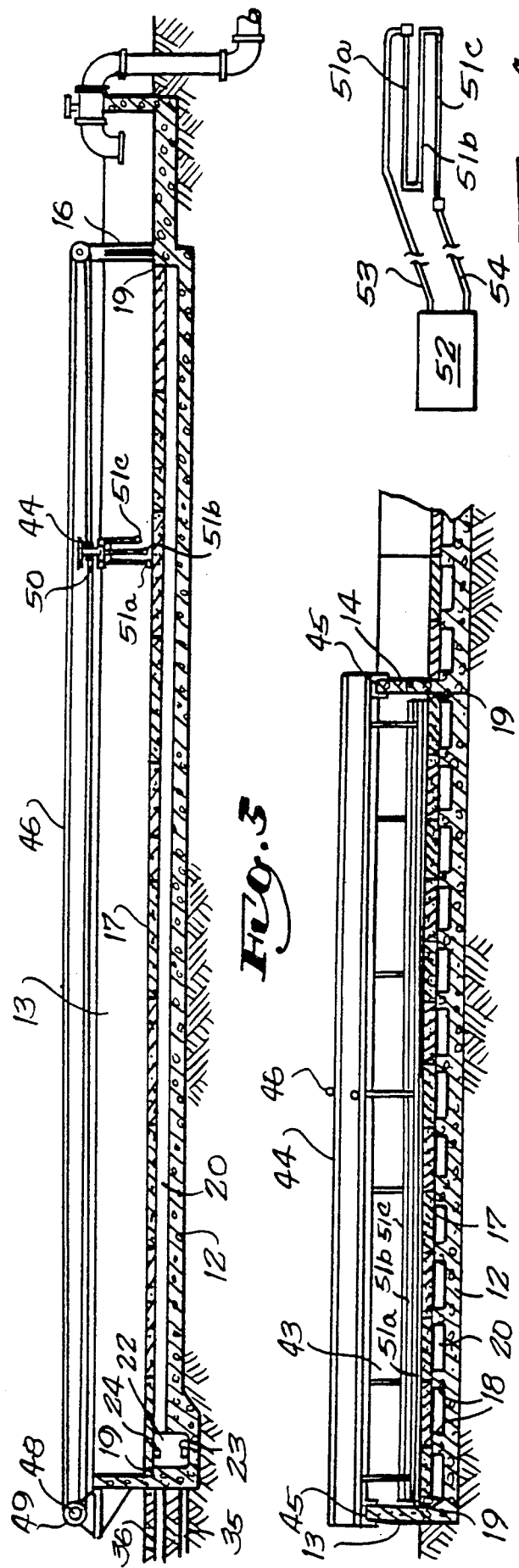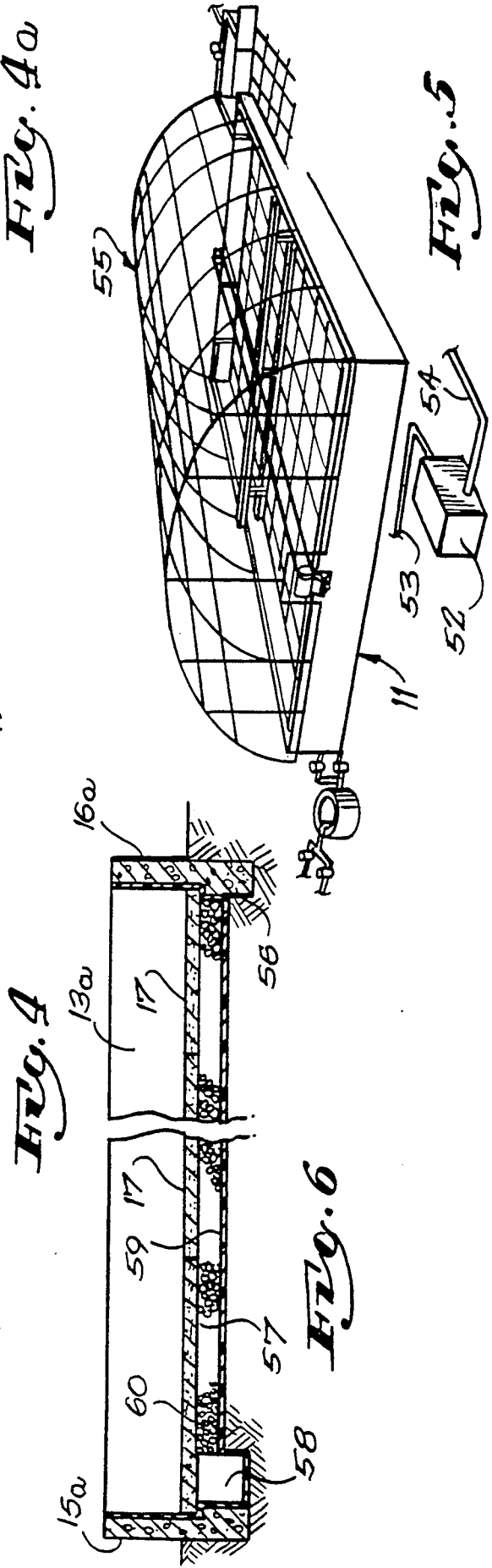

SLUDGE DEWATERING PROCESS USING MULTIPLE LAYER PLATE

This is a continuation of copending application Ser. No. 379,758, filed May 19, 1982, now abandoned, which is a division of copending Application Ser. No. 202,241, filed Oct. 30, 1980, now U.S. Pat. No. 4,382,863, which is a continuation of copending application Ser. No. 098,887, filed Nov. 30, 1979, now abandoned, which was a continuation of copending Application Ser. No. 930,529, filed Aug. 2, 1978, now abandoned, which was a continuation-in-part of copending Application Ser. No. 739,602, filed Nov. 8, 1976, now abandoned.

This invention relates to a sewage or water treatment system. The invention is directed particularly to improvements in rapid sludge dewatering or sludge reduction beds associated with such systems, and progressive removal of sludge cake as a continuing operation by mechanical means.

BACKGROUND OF THE ART

In the past, technological advances in the treatment of sewage have been directed for the most part to the various processes utilized in the reduction of raw sewage, such as aeration, settling coagulation, chemical precipitation of metallic ions, etc. The end products of all such sewage from water treatment facilities, however, are a clear effluent and waste sludge. This invention is directed particularly to novel and innovative means for the handling, processing, dewatering and disposal of such sludge in an efficient and economical manner.

The first requirement in sludge handling is to reduce moisture, and to increase handling ability by reducing volume. The process is usually referred to as concentration, thickening, dewatering or drying, according to the amount of moisture being removed. Different sewage and water treatment processes yield sludges of different solids concentrations ranging approximately from 2 to 20 percent. Further moisture reduction may be desirable to 25% solids for some types of mechanical handling. Higher solids content may be desirable for specific uses or disposal methods.

Existing sludge dewatering equipment falls primarily into two categories (1) simple and inexpensive, but slow, sand drying beds; and (2) fast, but expensive, highly mechanized devices such as presses, vacuum filters, centrifuges, heat dryers and incinerators.

Because of the increase in the separation of both free and bound water from the sludge solids effected by the instant invention, a 200% savings is realized in the area of land required for the dewatering process, and further savings in the operating and maintenance costs of sludge processing and utilization are experienced. No other sludge dewatering system is more cost effective and efficient in continued operation.

Sand drying beds require up to seven weeks to achieve cake concentrations of 25 to 40 percent. The slowness of this method requires bed areas ranging from 1 to 3 square feet per capita of population served, depending on sludge quality and climate conditions. The extensive land requirements of such systems have commonly forced plants serving more than 30,000 persons into mechanical equipment. Sand beds are, however, used by 38 percent to cities serving populations over 100,000.

The disadvantages of mechanical equipment stem from its high initial cost, high maintenance and operational costs, frequent breakdown problems and large energy consumption.

SUMMARY OF THE INVENTION

Among the objects of the sludge reduction system herein described is provision of a new and improved inexpensive system of sludge dewatering, drying, and disposal, without a high degree of mechanization, thus attaining fast, efficient drying with low land requirements, and maintaining low initial cost and maintenance simplicity.

Another object of the invention is provision of a new and improved system for sludge reduction of the character hereinabove described in which use is made of a plurality of adjacent filter beds utilizing cast filter plate or monolithic pour structure on a pervious sub-structure for supporting the plate and providing drainage for collection of the filtrate, the assemblage being of such strength and rigidity as to provide for passage thereover of free moving mechanized sludge handling equipment units such as front end loaders.

Another object of the invention is provision of a new and improved system making use of a precast retention filter plate for use in sludge reduction or dewatering beds and the like that is comprised of granular aggregate material such as silica sand, anthracite, or aluminum oxide and bonded by epoxy resin, the sand or other media being of such size and in such proportion with respect to the epoxy bonding agent as to provide optimum porosity for a high volume percolation rate suitable for sludge reduction, while at the same time exhibiting high tensile and compressive strength sufficient to support mechanical equipment and being substantially chemically inert.

Still another object of the invention is provision of a new and improved system for rapid sludge dewatering of the above nature including a simultaneous heating and moving device for the sludge being dewatered, and provision of a high vacuum which is applied in the void area below the rigid porous filter plate, thereby substantially enhancing the rate and degree of sludge dewatering or drying.

Another object of the invention is provision of a new and improved system, method and means for rapid sludge dewatering of the character described including solar heating of the sludge for accelerated drying and air pollution control. Further included among the objects is means for and processes of backwashing, vacuum drying, chemical treatment and chlorination of the sludge in the moisture reduction process.

A further object is provision in the basic design of the sludge dewatering system for disinfecting the sludge cake and the liquid filtrate by chemical or irradiative means.

It should be understood that this disclosure emphasizes certain specific embodiments of the inventive method, system and apparatus, and that all modifications or alternatives equivalent thereto are within the spirit or scope of the invention as set forth in the appended claims.

DESCRIPTION OF THE FIGURES

FIG. 3 is a longitudinal cross-sectional view, taken along the line 3—3 of FIG. 2 in the direction of the arrows;

FIG. 4 is a transverse cross-sectional view taken along the line 4—4 of FIG. 2 in the direction of the arrows;

FIG. 4A is a view in detail of the emersion heater steam supply assembly;

FIG. 5 is a perspective view similar to that of FIG. 1 but further illustrating the use of a transparent canopy for keeping out rain, high humidity, snow etc., and for capturing solar heat and retaining it;

FIG. 6 is a longitudinal cross-sectional view similar to that of FIG. 3 but illustrating an alternative support and drainage structure for the modular unit filter plates;

FIG. 7 is a schematic diagram of the sludge reduction system illustrating its interrelation with a typical sewage treatment plant;

DESCRIPTION OF THE PREFERRED EMBODIMENT

Figure 1:
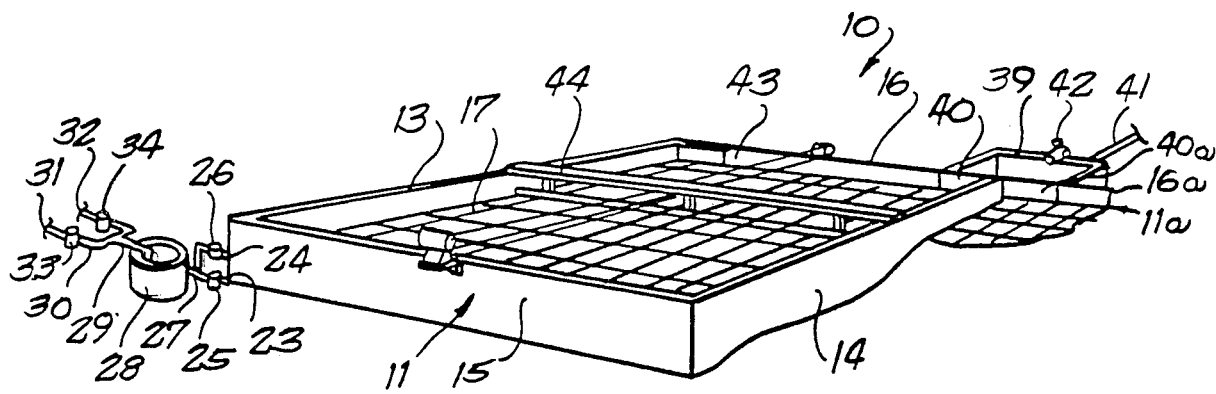
FIG. 1 is a perspective view of a sludge reduction or dewatering bed embodying the invention.

Described below is an embodiment of the inventive apparatus chosen for purposes of illustration as the environment for the practice of the inventive method.

There is a typical 2-unit sludge reduction bed 10. A first unit 11 is shown in its entirety and a second unit is only partially illustrated. As illustrated in FIGS. 1 through 4, each bed unit 11 comprises a shallow, open-topped, box-like sludge container for receiving sludge to be chemically pretreated and processed. The sludge container is integrally formed of monolithically poured, reinforced concrete, or alternatively, it could be fabricated of other structural materials such as fiberglass, concrete blocks, steel, etc. The container comprises a bottom slab portion 12, upstanding sidewall portions 13 and 14, and upstanding front and back wall portions 15 and 16, respectively. The internal dimensions of each sludge container unit 11 may, for example, be 20×40 feet to provide in one form of the invention for the close fitting assembly therein of a plurality of modular filter plates 17 which may conveniently be 2 ft. ×4 ft. in size, for example. The sludge containers are made impervious by float finishing or by the use of concrete additives, or a suitable sealer, thereby preventing pollution of the subsoil by leakage of the filtrate.

The plates 17 or monolithic poured slab serves as the filtering media in the sludge dewatering or reduction process, and is sufficiently strong to withstand pressures imposed by mechanized dried sludge handling equipment which will be driven over the bed from time to time for the removal of the sludge cake at the end of the rapid sludge dewatering process.

The above described rigid filter plate is reinforced with inert glass fibers providing the required strength or durability during daily mechanical unloading. The filter plate is preferably installed over a mass 60 of large size clean aggregate (¾" to 1½") which is keyed together by a vibratory compactor during construction. After keying, the aggregate is given a light coating of sprayed-on epoxy to prevent movement of the aggregate during daily unloading of the dewatered and dried sludge cake by mechanical means. Above the aggregate 60 is a leveling layer 60' of 6-10 sand, also keyed and sprayed with epoxy. The aggregate and leveling layer thus installed to a depth of 12" to 24" inside the outer impervious shell provides a void area of approximately 40% where the vacuum is uniformly applied over the whole poured filter media underdrive. This void area also provides a reservoir for the water filtrate during the filling-up operation. Should a power failure occur, the same area serves to collect all the filtrate.

The bottom slab portion 12 of the sludge container unit 11 in the alternative may be integrally formed with a plurality of equidistantly-spaced, parallel longitudinally-extending ribs 18, said ribs being approximately square in cross-section and having upper surface portions lying in the same horizontal plane. The ribs 18 are so spaced as to support marginal longitudinal underside portions of adjacent rows of the filter plates 17.

As illustrated in FIGS. 3 and 4 the upstanding sidewall portions 15 and 16 are each formed with inwardly directed ledges 19 defining shoulders at the same height as that of the ribs 18 for the support of outer marginal edge portions, at the underside of the peripherally positioned filter plates 17. Thus, as illustrated in FIG. 4, each of the longitudinally-extending fluid and gas flow chambers serve as a through passage for sludge filtrate, for backwash, or for vacuum voiding, as is hereinafter more particularly described.

As further illustrated in FIGS. 3 and 4, the upper surface of the bottom slab portion 12 of the sludge container 11 is sloped downwardly from back to front so as to provide for gravity drainage of sludge filtrate or processing fluids into a transversely-extending manifold 22 formed within the sludge container.

Figure 2:
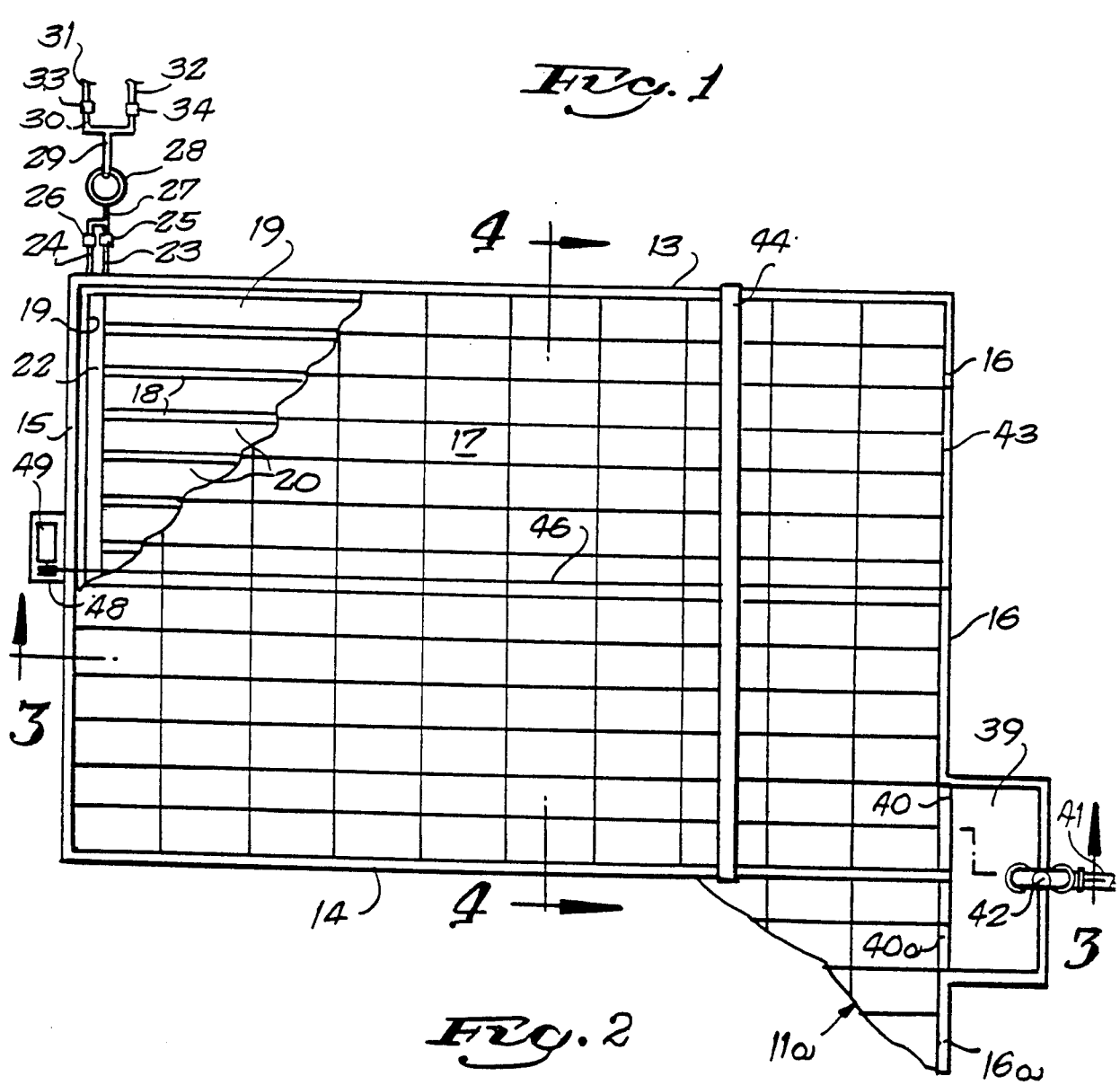
FIG. 2 is a top plan view.
Figure 2:
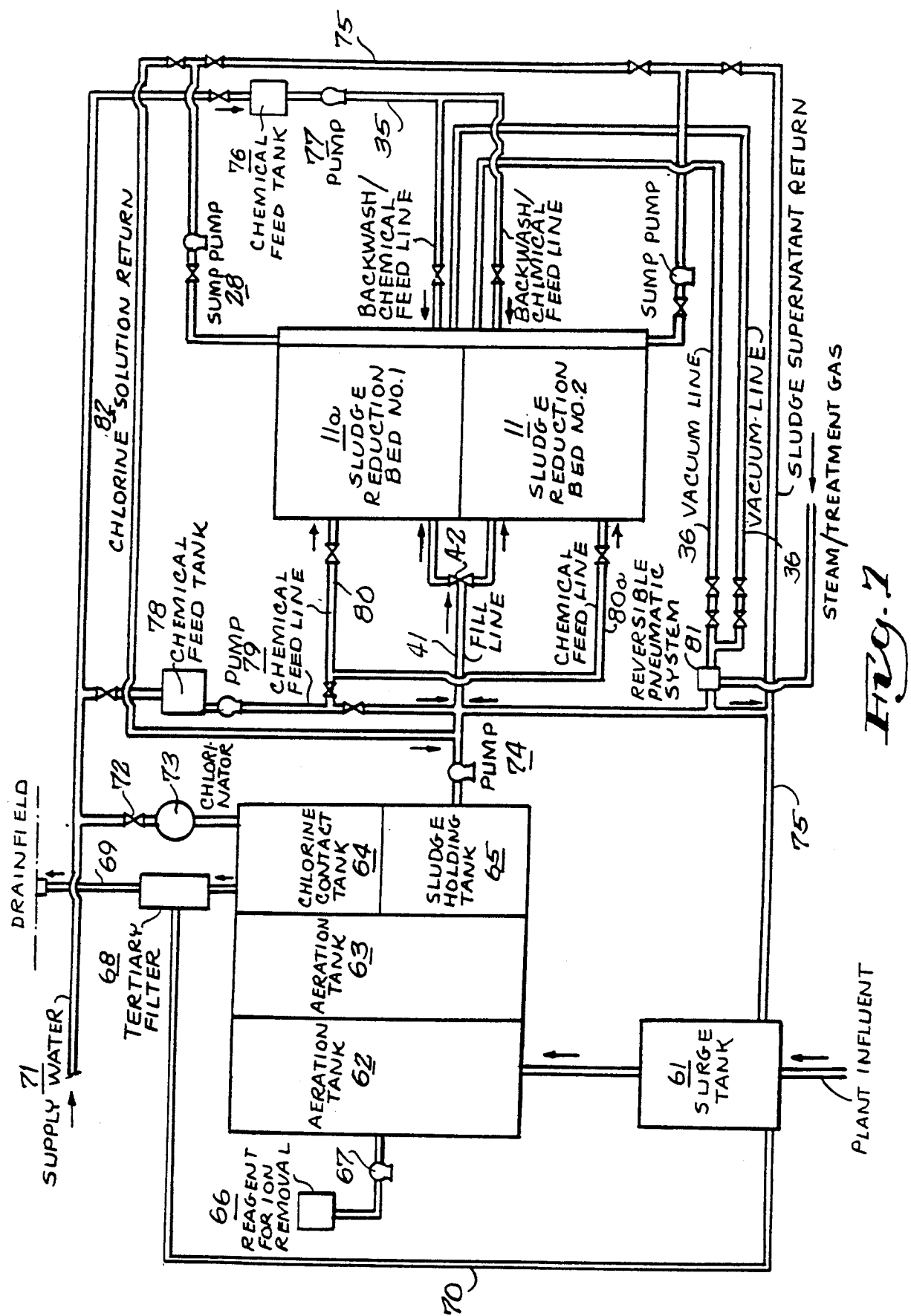

Drainage of the sludge container 11 is provided for by a manifold fluid conduit 23 communicating with the bottom of the manifold 22 and extending outwardly of the upstanding sidewall 13. There is a gas conduit 24 also extending through the sidewall 13 at the top of the manifold. The manifold and conduits 23 and 24 extend through individual electric control valves 25 and 26 to join at a common inlet conduit 27 leading to a sump pump 28. The output of the sump pump 28 is fed through conduits 29 and 30 to sludge filtrate return line 31 and chemical solution return line 32, respectively, as controlled by respective control valves 33 and 34, as shown in FIGS. 1 and 2. As many as four or more rapid sludge dewatering units, if desired, may be connected in a basic design to one central vacuum reservoir and effluent tank by means of cross-connecting lines and control valves, thereby conserving material and capital investment.

Means is provided for filling one or the other or both of the side-by-side sludge container units 11, 11a, comprising the two-unit sludge reduction bed 10, with fluid waste sludge. To this end, adjacent zones of the backwall portion 16 of the side-by-side sludge containers 11, 11a are joined by a rearwardly-extending sludge-receiving filling and mixing box 39. Slide gates 40 and 40a in respective backwall portions 16 and 16a permit selective passage of liquid sludge fed into the filling and mixing box 39 into one of the other or both of the sludge containers 11 and 11a selectively, depending upon the volume of sludge being fed into the beds for treatment. A comparatively large diameter conduit 41 discharges through a manually controlled valve 42 into the filling and mixing box 39, said sludge being pumped from a typical sewage or water treatment facility for disposal.

Although not shown in the drawings, an important factor in the practice of the method herein disclosed is a conventional mobile mechanized vehicle capable of entering on the filter plate, there to be loaded with sludge cake for removal. Such mobile units are commercially available and if not already equipped with a scraper and lifting mechanism, accessories of such description can be installed.

Mobile mechanized units most advantageous for use in the system here disclosed are four wheel vehicles of sufficient length and breadth to carry the operator and an appreciable load of sludge cake. With wheels providing traction, the operator can mount and drive to and from a loading location on the filter plate. It is of consequence, therefore, that the length and breadth of each sludge container 11, 11a be as large as described to allow the mobile unit to move about while the sludge cake is being scraped clear from the top surface of the filter plate, and ultimately loaded on the mobile unit for transportation elsewhere.

The nature of the mechanized units is clearly such that care must be taken in construction of the filter plate and its support to carry the load of the mobile mechanized unit and facilitate repeated cleaning and scraping cycles for removal of sludge cake when dried, while avoiding damage to the filter plate's upper surface.

Clearly, because of the semifluid character of the sludge, side, front and back wall portions 13, 14, 15 and 16 must provide a liquid-tight container while the dewatering of the sludge is taking place. To accommodate entrance and exit of the mobile mechanized units, a slide gate, such as gate 43, is provided in the back wall portion 16 of the sludge container unit 11. A similar gate (not shown) is provided for the back wall 16a of the sludge container unit 11a and for each of any additional sludge container units which may make up an installation. Accordingly the gate must have a liquid tight fit when closed, and provide an opening wide enough to accommodate a loaded mobile mechanized unit such, for example, as a front end loader.

Optional means is provided for simultaneously heating and moving sludge in the sludge container units 11 and 11a during the dewatering process. This system will provide for a 7% solid sludge cake content thereby facilitating prolongation of the drying process to achieve a drier condition. In other words, by closing the cracks in the sludge as it starts to crack at 7%, the sludge heating and moving means serve to extend the dewatering process, thus producing drier sludge cake in a shorter time.

More specifically, there is a transverse support bar 44 which straddles the upstanding sidewall portions 13 and 14 of each of the sludge container units 11 and 11a. The ends of the support bar 44 carry roller bearings 45 which ride along the upper surfaces of the sludge container sidewall portions 13 and 14 to minimize frictional resistance in the movement of said support bar reciprocatively between the front and backwall portions 15 and 16, respectively, of the associated sludge container unit.

A continuous drive cable 46 is looped between an idler pulley 47 upstanding from and fixed with respect to the center of the backwall portion 16 and the drive pulley 48 of a reversible electric motor 49. The electric motor is fixed with respect to and extends upwardly of a central portion of the container front wall portion 15.

The lower loop portion or run of the drive cable 46 extends through and is attached to a central portion of the transverse support bar 44, as indicated at 50 in FIG. 3. The transverse support bar 44 carries a plurality, three in the embodiment illustrated, of transversely-extending emersion heater conduits 51a, 51b and 51c. The conduits are positioned at various heights to extend at various levels into the semifluid mass of sludge fed into a sludge container 11 for treatment.

As illustrated schematically in FIG. 4a, a steam generator 52 supplies superheated steam through the emersion heater conduits 51a, 51b, and 51c, connected in series, through flexible conduits 53 and 54. An electric energization circuit (not shown) for the reversible drive motor 49 serves to reciprocatively move the transverse support bar 44 and its associated emersion heater conduits back and forh within the sludge container units 11 and 11a during the sludge dewatering or drying process. Alternatively, elongated electric heating units could be used.

The sludge moving and heating means, comprising the reciprocative transverse support bar 44 and its associated emersion heater conduits 51a, 51b and 51c, serves primarily as a device for uniformly moving the sludge to minimize any tendency to the formation of shrinkage cracks therein, particularly during the vacuum drying process. The sludge, being a gelatinous mass, is much more easily cut for mixing by the heated conduits as compared with unheated conduits, to which the sludge would have tendency to stick. The heat imparted to the sludge being mixed also renders it more fluid, particularly in cold weather, thereby further enhancing the time efficiency of the vacuum drying process.

An important feature of the invention resides in the composition of the filter plates 17. They must not only exhibit the requisite porosity for rapid and efficient filtering, be inert with respect to reaction with any of the various caustic and corrosive chemicals found in sludge and sludge treatment, but must also withstand loads imposed by the mobile mechanical units employed to remove the dried sludge cake. It has been established that a 3" thick filter plate having the required strength, resistance to chemicals and filtering or percolation rate is obtained with a mixture of angular silica filter sand having a sieve size of between 6 and 10 millimeters used as the aggregate, and a bonding agent of chatahoochie epoxy in the ratio of one pound of the epoxy to 20 pounds of the aggregate.

Figure 11:
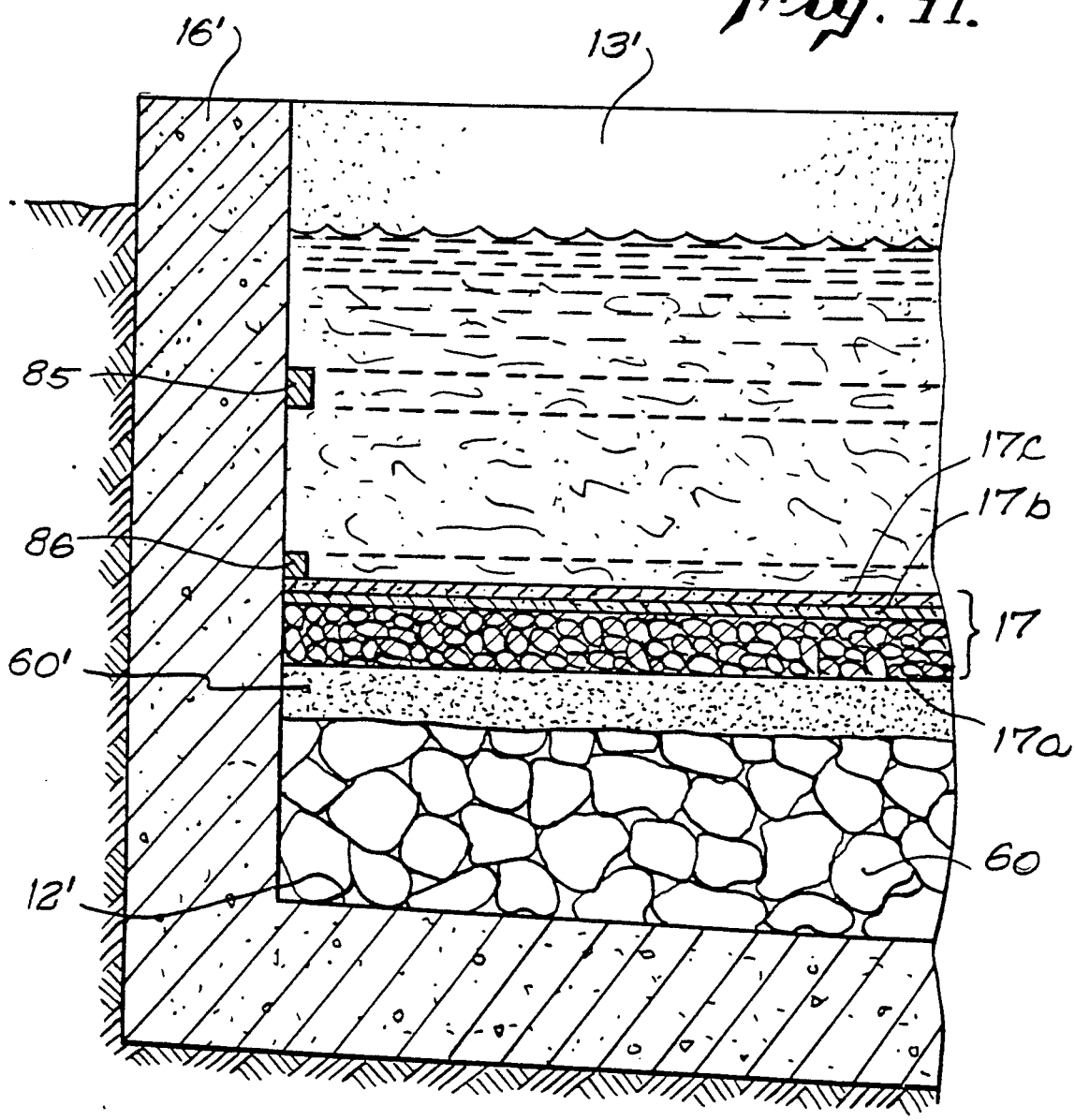
FIG. 11 is an enlarged sectional view on the circular line 11 of FIG. 10.

An effective filter plate is shown in FIG. 11 of the drawings. The plate 17, whether individual plates or a poured slab, is 1½ to 2 inches thick and has a lower permeable layer 17a of ¾ inch to 1½ inches of aggregate. This is rigidified, meaning that the particles are worked into a mass such that they are substantially all interlocked with each other, to inhibit any further shifting or movement. The choice of aggregate is such, however, that the layer remains permeable and permits free flow of water withdrawn during the dewatering cycle.

Above the lower permeable layer is a stratum comprising a leveling layer and an uppermost layer. The leveling layer 17b is of about ¼" thickness of which 6–20 sand is suitable. This leveling layer 17b is also rigidified by working or tamping similar to, and for the same purpose as, the lower permeable layer, leaving it firm, and at the same time, permeable.

Above the leveling layer is an uppermost layer 17c of sharp, fine 16 grit anthracite and/or aluminum oxide aggregate also rigidified through permeable. Individual sharp points of the 16 grit anthracite and/or aluminum oxide present a "sand paper" like character for the upper surface of the plate 17. Included in all the layers is an appropriate binder such as epoxy, which, after hardening, renders the multilayered filter plate monolithic and physically strong to be heavy equipment traffic rated as described.

The columnar structure 60, 60', whether gravel as shown in FIG. 11, or ribs, resting on the impermeable bottom slab portion 12, substantially as has been already described, leveled off by the layer 60' of 6–10 sand, supports the filter plate 17 at a location within wall portions 13, 14, 15 and 16.

In a second form of the invention shown in FIG. 5, a transparent canopy 55 extends over the sludge container 11, fully enclosing the same, thereby serving not only as a rain water shed, but also providing for capturing solar heat to accelerate the sludge drying process. The canopy may also serve to contain heat generated by fuel-fired heaters. Preferably, the canopy may be of a dark colored vinyl sheet of the type commonly used in hothouses to create the so-called greenhouse effect. The canopy also serves to contain gaseous pollutants, often malodorous, which might otherwise contaminate the surrounding atmosphere. These gaseous pollutants can be recycled to the primary treatment facility from which the sludge is obtained for sludge reduction, to be reabsorbed in the fluid state. Solar heat collector panels provide warm dry air to be pulled through while the vacuum below is applying an accelerating dewatering assist.

By heating air in the space above the sludge bed, whether by solar energy in the event a canopy is employed, or by some other appropriate heater, multiple benefits result. Warm air when drawn through the filter plate with the filtrate appreciably accelerates drying of the sludge cake.

The drawing of warm air warms the semi-liquid sludge and accelerates the coagulating of the mass which, at the same time, accelerates the dewatering process, and, consequently, the drying of residue.

Occasionally reversing air flow through the filter plate has added benefits, namely loosening up the accumulation of partially dewatered sludge, as well as enhancing the dewatering cycle.

FIG. 6 is a longitudinal cross-sectional view, similar to that of FIG. 3 but with portions broken away, illustrating a simplified form of sludge container embodying the invention. The structure there shown is one particularly well-suited for installation on land area having high bearing strength such as coral rock or naturally dense sand or sand and rock mixtures. Under such conditions, as illustrated in FIG. 6, the impervious concrete bottom slab can be eliminated and the upstanding sidewalls 13a and front and backwall portions 15a and 16a can be integrally formed of reinforced poured concrete with a peripheral footing 56.

As further illustrated in FIG. 6 and as indicated at 57, the interior bottom surface will be sloped for drainage from back to front into a recessed, transversely-extending manifold 58 corresponding with the manifold 22 of the embodiment illustrated in FIGS. 1 through 4. A moisture impervious layer 59 of 12 gauge Neoprene sheeting may cover the interior of the sludge container thus formed. The two to four inch thick layer of coarse clean gravel 60 on the bottom area of the Neoprene sheeting 59 presents a horizontal upper bearing surface upon which the filter blocks 17 are placed, as in the embodiment of the invention illustrated in FIGS. 1 through 4. Preferably, the gravel will be of a sieve size from ¾ to 1 inch.

The spaces within the mass of gravel form a continuous flow passage for filtrate which passes through the filter plate. Accordingly the gravel serves a double purpose, namely, that of establishing flow passages and that of acting as a columnar support for the filter plates throughout the area of the sludge container unit.

Instead of using modular plates 17, the filtering medium can be a single monolithic slab (not shown) of the silica sand and epoxy binding agent mixture. Gravel is effective for use as a combined support and structure forming flow passages. The monolithic slab may be supported by ¾" to 1½" aggregate, providing for the approximately 40% void area, or by ribs like the ribs 18 of FIGS. 1 and 4. The use and operation of the invention illustrated in FIG. 6 is otherwise the same as the principal embodiment of FIGS. 1 through 4.

FIG. 7 illustrates, schematically, a typical sewage treatment plant and associated two-unit sludge reduction system embodying the invention. The sewage treatment system may comprise, for example, the usual raw sewage input surge tank 61 feeding successive aeration, settling and chlorine contact tanks 62, 63 and 64, respectively, which serve to reduce the solid matter to a substantially homogeneous sludge discharged to a sludge holding tank 65.

Reagent for ion removal is supplied to the aeration tank 62 from a supply tank 66 through a pump 67. Effluent is passed from the chlorine contact tank 64 to a tertiary filter 68 for further removal of suspended solids, and the filtered effluent is discharged through conduit 69 to a drain field or other suitable means of disposal. The filtered solids are returned through conduit 70 to the surge tank 61 for reprocessing and eventual disposal in the sludge.

Supply water is fed through conduit 71 and control valve 72 into a chlorinator 73 discharging chlorine in solution into the chlorine contact tank 64 for treatment of the effluent therein. The water supply line 71 also serves to feed chemicals in solution to the sludge container units 11, 11a in the sludge treatment process.

In operation of the sludge dewatering or reduction system in the embodiment illustrated in FIGS. 1 through 4 and 7, fluid sludge to be treated is pumped through a sludge pump 74, conduit 41 and control valve 42 into the common sludge filling and mixing box 39, wherein it will mix to a more or less homogeneous mass, then allowed to flow into one or the other or both of the sludge container units 11 and 11a by appropriately opening the sludge gates 40 and 40a respectively. The sludge container units 11 and 11a will be filled to a depth of approximately 12 inches, whereupon the liquid fraction of sludge will begin to percolate through the filter plates 17 and drain into the manifold 22 at the front of the unit. This separated filtrate will ordinarily be returned by the sump pumps 28 to the surge tank 61 through appropriately valved conduits 75 for retreatment (see FIG. 7).

Various forms of treatment of the sludge in the sludge reduction units is provided for, depending upon the quality of the sludge to be treated. For example, washing with clean water or elutriation may be required of sludges high in soluble inhibitors of coagulation. To this end, supply water fed through conduit 71 and passing through chemical feed tank 76 is pumped into backwash chemical feed line 35 by backwash pump 77. Sludges rich in greases may require lime conditioning. Industrial waste sludges may require other chemical conditionings which can be supplied as a backwash solution by adding appropriate chemicals to the chemical feed tank 76. Alternatively, chemical treatment solutions can be added directly to the sludge by passing supply water solvent through a chemical feed tank 78 and pump 79 to conduit 80 and 80a discharging into the sludge container units 11 and 11a respectively.

It is also to be understood that cracking of the sludge cake during vacuum drying can also be inhibited by the use of chemical coagulants added to the sludge at the filling pump.

In following a cyclical pattern for adjacent sludge beds the process includes pretreating raw sewage with a polymer coagulant to break up solids and flocculate the sludge particles. Numerous tests dictate that the sludge be treated to create large soft particles and soft particles of various molecular and sieve sizes. The larger particles gain weight and then bring heavy are settled first. Smaller finer particles are settled thereafter and are trapped by the already settled larger particles. Settling of the particles is assisted by application of a vacuum beneath the filter plate.

The added coagulant, by flocculating the sludge, causes formation of soft particles or masses of various sizes. As stated, the larger particles tend to settle first by gravity action and spread a gel-like slime layer over the top of the filter plate. Free water drains rapidly through the relatively large porous spaces of the initially formed layer, and through the filter plate. This initially formed layer at the same time traps the smaller particles which continue to settle out.

When a vacuum is applied as a next step, a fast liquid filtrate flow is induced through the porous sludge cake and the filter plate, rapidly dewatering the sludge.

The choice of anthracite and/or aluminum oxide for the top layer of the monolithic filter plate is of significance. Anthracite and/or aluminum oxide provides sharp, upwardly extending points and these tend to pierce the material of the larger particles in the slime layer adding to the speed and completeness of the dewatering.

A circumstance of some note is that a vacuum applied quickly after formation of the flocculated slime expedites formation of the cake. This is directly opposite to the cake formation in a standard vacuum filter, in which the smaller particles are picked up first in the cake or, at best, a homogeneous sludge cake is achieved thus forming a sludge cake which is more permeable and harder to dewater. Wide latitude is possible in strength of the vacuum applied which may vary with circumstances between 1 and 27 inches. The sludge cake will continue to dry while water is pulled from the floc. This differential type of cake formation produces a thicker cake and delays formation of cracks, permitting the maintenance of the vacuum for a longer period. In many cases, this is as far as the dewatering need go for quick and economical disposal since 75 to 80% of the water will have been removed. A final optional stage can be the further dewatering of the sludge cake by during the adherent water by hot air pulled by a vacuum with or without mechanical raking.

Pneumatic lines 36 extend from the sludge container sumps to a reversible pneumatic system 81 which, when operated in its vacuum mode, provides a substantially reduced pressure beneath the filter plates 17, thereby greatly accelerating the dewatering process. An added benefit of applied vacuum will be the suctioning for in-plant disposal of any undesirable gases and odors. This vacuum drawn filtrate will normally be returned to the sewage treatment facility surge tank 61 for reprocessing along with the gravity filtered or percolated filtrate.

Figure 8:
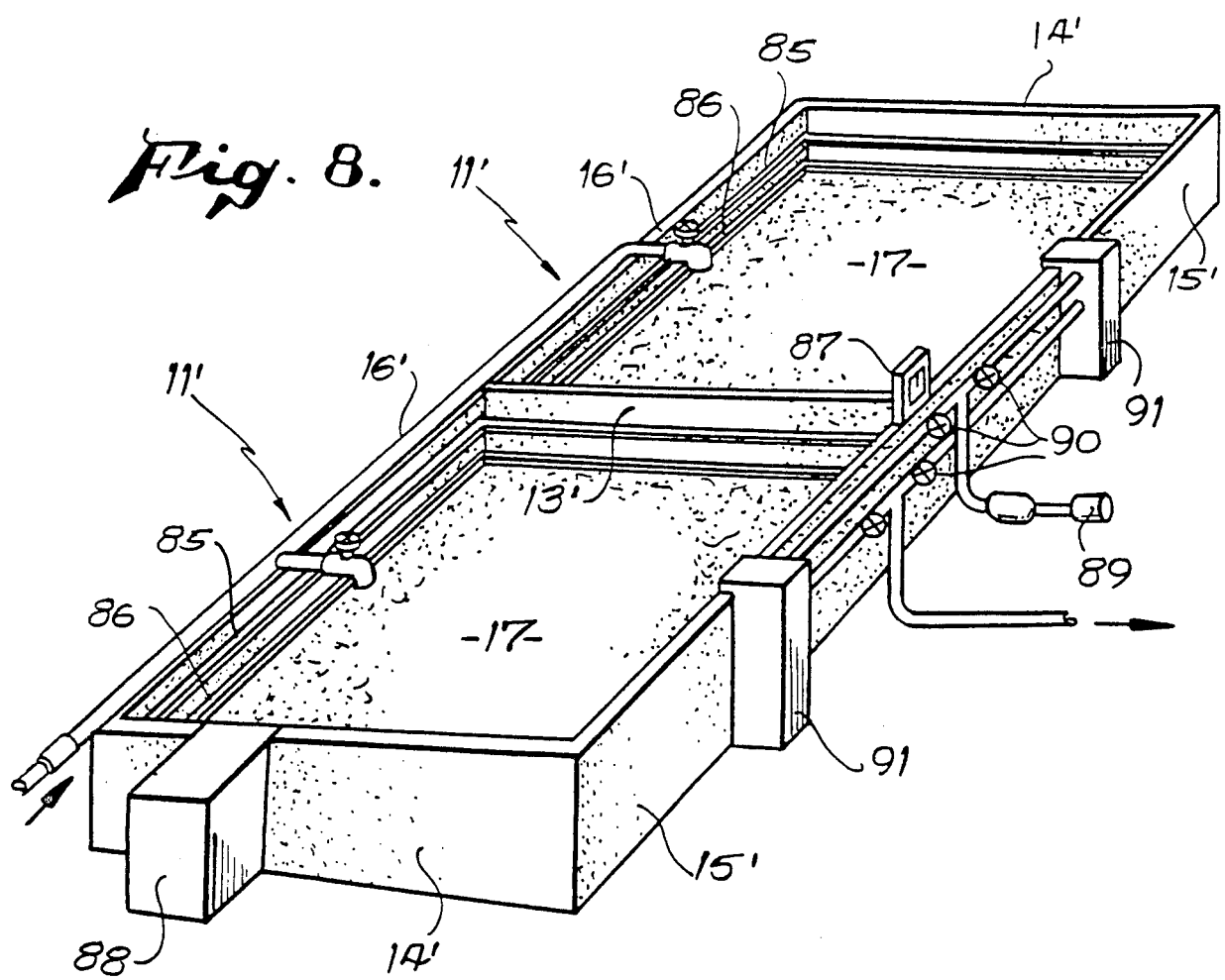
FIG. 8 is a side perspective view of a representative pair of sludge reduction beds equipped for electroosmosis.
Figure 9:
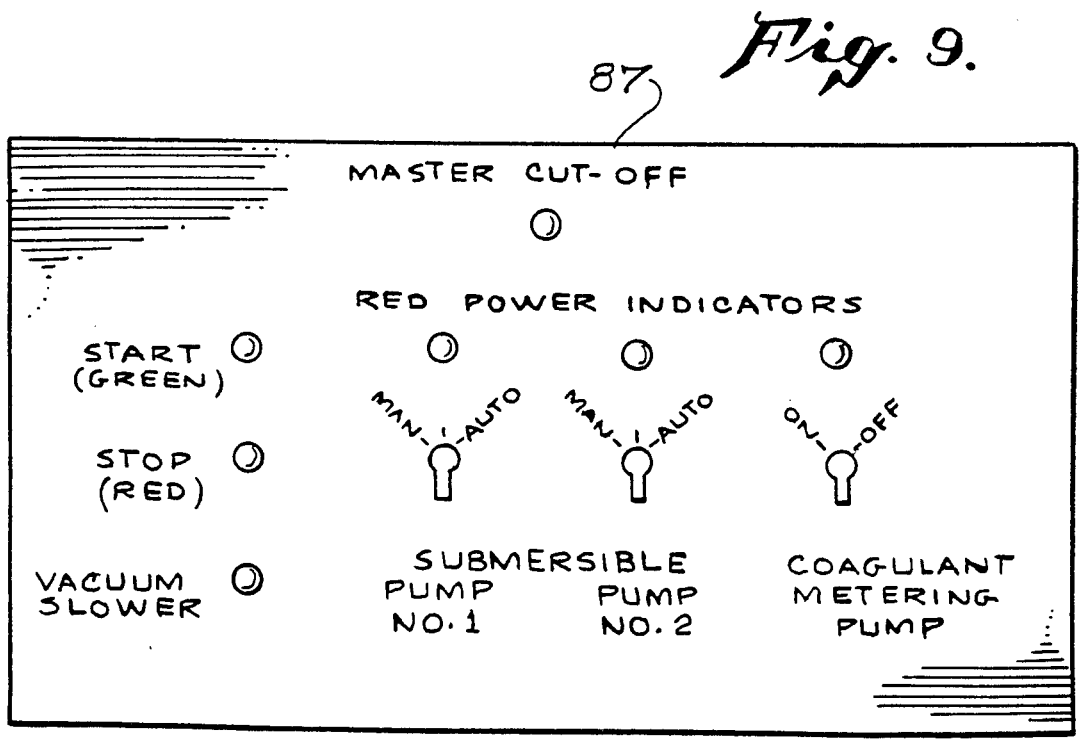
FIG. 9 is an elevational view of the control panel.
Figure 10:
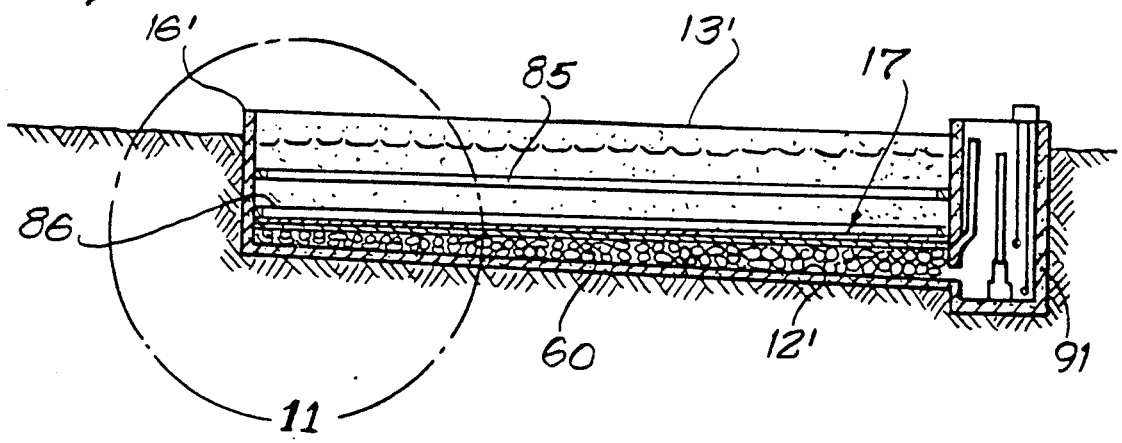
FIG. 10 is a cross-sectional view of one of the beds of FIG. 8.

In FIG. 8 is shown a pair of sludge containers 11' connected in tandem utilizing common sidewall 13'. In other respects the containers are identical each comprising, as shown, a second side wall 14' with front wall and back wall portions 15' and 16', respectively, surrounding an impervious bottom slab 12'. The customary monolithic filter plate 17 is here shown extending over the entire upper surface of a level, rigidified supporting course 60 of aggregate.

Of special consequence in this form of the invention is the presence of an anode 85 and cathode 86. Where the side walls of the container 11' are to be about 12" high above the filter plate the anode is fastened to the wall structure about 4" above the top level of the filter plate. The anode is preferably copper and located so as to be continuously immersed in the semi-liquid sludge.

This anode extends around all four side walls.

The cathode 86, likewise extending around all four side walls, is located at the bottom of the body of semi-liquid sludge, preferably at and touching the monolithic filter plate itself. The material of the cathode is non-ferrous and a material other than copper. Carbon is found to be satisfactory. An appropriate non-ferrous metal may be, for example, zinc or aluminum.

The anode and cathode are not connected to any source of electric power but serve, instead, as anode and cathode in a bath of electrolite, as for example, the semi-liquid sludge. In this arrangement the electrodes establish an electroosmosis of the sludge causing the solid sludge particles to flow to the cathode and the water molecules to flow to the anode. The flow of water thus induced accelerates the speed of dewatering and, in fact, significantly contributes to the increased speed and completeness of dewatering and formation of sludge cake. Details of construction of the electrodes have not been included in the disclosure inasmuch as such details may vary considerably without departing from the scope of the invention.

For convenience there is shown a control panel with appropriate instrumentation 87 which has controls to motivate the sundry mechanical means such as the coagulant metering pump 88, blower control 89, valves for the various lines and the sump pump and vacuum chambers 91.

Following dewatering, isotope irradiation or addition of a chlorine solution may be employed to disinfect and deodorize the reduced sludge. This can be effected by supplying chlorine to the chemical feed tanks 76, 78 for backwash or forwardwash. An appropriately valved chlorine solution return line 82 provides for recycling the chlorine solution through the sludge as pumped by sump pumps 28 for efficient use of the chlorine. It will be understood that the various above described filtration, backwash and chemical treatment steps, both liquid and gaseous, in the sludge reduction process can be programmed for automatic operation, with selective variations depending upon the quality of the sludge to be dewatered or reduced.

Among the advantages of the sludge reduction dewatering system embodying the invention are the following:

1. Sludge having a dry solids content of 2% can be dewatered in approximately five hours sufficiently to be removed from the sludge containers mechanically and transferred by open truck to a disposal site without difficulty or loss.
2. Sludge can be dewatered to 15% dry solids in approximately eight hours.
3. Recapture of approximately 99.5% of the solids in the sludge reduction process.
4. Chemical disinfecting of the dry sludge is easily effected.
5. Disinfection by isotope irradiation.
6. At least 40 times less land area is required as compared with sludge dewatering systems heretofore employed.
7. Substantial reduction in odor pollution of the surrounding atmosphere.

Having described the invention, what is claimed and sought to be secured by Letters Patent is:

1. In a process for dewatering sludge on a filter plate, wherein the improvement comprises the following steps in combination:
   (a) placing the sludge on a stratum of a filter plate having multiple layers, the filter plate comprising a stratum and a lower support layer,
      i. the stratum comprising particles of sand and an epoxy for rigidly bonding the particles together to define the stratum, the particles being of sizes that do not impede high volume percolation, and the epoxy being present in an amount that does not impede high volume percolation;
      ii. the lower support layer comprising aggregate material and an epoxy for rigidly bonding the aggregate material together to define the lower support layer, the aggregate material being of sizes that are greater than the sizes of the particles in the stratum and that does not impede high volume percolation, and the epoxy being present in an amount that does not impede high volume percolation; the multiple layers of the filter plate being monolithically bonded together with an epoxy and the filter plate being of sufficient structural strength to support mobile mechanized sludge removal means;
   (b) permitting filtrate from the sludge to percolate through the filter plate until the sludge is dewatered to an extent making it removable by sludge removal means; and
   (c) removing the dewatered sludge from the stratum by sludge removal means.

2. A process as in claim 1 wherein the lower support layer defines a thickness of between about $\frac{3}{4}$ and about $1\frac{1}{2}$ inches.

3. A process as in claim 1 wherein the plate is reinforced.

4. The process of claim 1 wherein the sludge is pretreated with a chemical conditioner to flocculate the sludge.

5. The process of claim 1 wherein the stratum comprises an uppermost layer and a leveling layer.

6. A process as in claim 5 wherein the uppermost layer defines a thickness of between about $\frac{1}{4}$ and about 1 inch.

7. A process as in claim 5 wherein the uppermost layer defines a thickness of between about $\frac{1}{4}$ and about 1 inch and the lower support layer defines a thickness of between about $\frac{3}{4}$ and about $1\frac{1}{2}$ inches.

* * * * *